US010159720B2

(12) United States Patent
Ilan et al.

(10) Patent No.: US 10,159,720 B2
(45) Date of Patent: Dec. 25, 2018

(54) THROMBIN MICROCAPSULES, PREPARATION AND USES THEREOF

(71) Applicant: Omrix Biopharmaceuticals Ltd., Rehovot (IL)

(72) Inventors: Erez Ilan, Kibbutz Netzer Sereni (IL); Assaf Gershonovitch, Kfar-Saba (IL); Rivka Kaufman, Haifa (IL)

(73) Assignee: Omrix Biopharmaceuticals LTD, Rehovot (IL)

( * ) Notice: Subject to any disclaimer, the term of this patent is extended or adjusted under 35 U.S.C. 154(b) by 0 days.

(21) Appl. No.: 15/366,287

(22) Filed: Dec. 1, 2016

(65) Prior Publication Data

US 2017/0157222 A1 Jun. 8, 2017

Related U.S. Application Data

(60) Provisional application No. 62/264,432, filed on Dec. 8, 2015.

(51) Int. Cl.
*A61K 9/16* (2006.01)
*A61K 38/48* (2006.01)
*A61K 38/36* (2006.01)

(52) U.S. Cl.
CPC ............ *A61K 38/4833* (2013.01); *A61K 9/16* (2013.01); *A61K 9/1623* (2013.01); *A61K 9/1658* (2013.01); *A61K 9/1682* (2013.01); *A61K 38/363* (2013.01); *C12Y 304/21005* (2013.01)

(58) Field of Classification Search
CPC .......................... A61K 9/1647; A61K 9/1277
See application file for complete search history.

(56) References Cited

U.S. PATENT DOCUMENTS

| | | | |
|---|---|---|---|
| 6,113,948 A | 9/2000 | Heath et al. | |
| 6,121,232 A | 9/2000 | Nur et al. | |
| 6,416,739 B1 | 7/2002 | Rogerson et al. | |
| 6,703,047 B2 | 3/2004 | Sawhney et al. | |
| 7,125,569 B2 | 10/2006 | Nur et al. | |
| 8,846,105 B2 | 9/2014 | Koopman et al. | |
| 9,084,728 B2 * | 7/2015 | Goessl | A61K 9/0014 |
| 2010/0150900 A1 * | 6/2010 | Whitfield | A61K 9/5084 424/94.64 |
| 2010/0249044 A1 | 9/2010 | Walker | |
| 2012/0121532 A1 | 5/2012 | Goessl et al. | |
| 2012/0315305 A1 | 12/2012 | Koopman et al. | |
| 2015/0147312 A1 | 5/2015 | Ilan et al. | |

FOREIGN PATENT DOCUMENTS

| | | |
|---|---|---|
| EP | 071338861 | 5/1999 |
| WO | WO 1992/018164 | 10/1992 |
| WO | WO 1998/033533 | 8/1998 |

(Continued)

OTHER PUBLICATIONS

Chang, B.S. et al 'Enzyme thermostabilization by bovine serum albumin and other proteins: evidence hydrophobic interactions' Biotechnol Appl Biochem. (1995) 22 pp. 203-214.

(Continued)

*Primary Examiner* — Carlos A Azpuru
(74) *Attorney, Agent, or Firm* — David R. Crichton

(57) ABSTRACT

Provided are spray-dried thrombin powders comprising microcapsules, methods of preparation and uses thereof.

18 Claims, 5 Drawing Sheets

(56) References Cited

FOREIGN PATENT DOCUMENTS

| WO | WO 2002/095019 | 11/2002 |
| WO | WO 2007/117237 | 10/2007 |
| WO | WO 2011/151386 | 12/2011 |
| WO | WO 2014/135689 | 9/2014 |

OTHER PUBLICATIONS

Goncalves, H.B. et al 'Extracellular β-fructifuranosidase from Fusarium graminearum: stability of the spray-dried enzyme in the presence of different carbohydrates' Journal of Microencapsul. (2013) 30(7) pp. 624-631.

Pattnayak, P. 'Excipient Mediated Biostabilization of Protein Using Spray Drying Technique'—Thesis work done by Priyadarsini Pattnayak for a degree of master of technology, Biotechnology and medical engineering, under the guidance of Prof. Gyana Ranjan Satpathy, National Institute of Technology, Rourkela, India. Sep. 2010, 97 pages.

International Search Report re: PCT/IL2016/000024 dated Mar. 7, 2017.

* cited by examiner

THROMBIN MICROCAPSULES, PREPARATION AND USES THEREOF

FIELD OF THE INVENTION

The invention relates to the field of pharmaceuticals, and more specifically to a spray-dried thrombin powder comprising microcapsules, methods of preparation thereof and uses thereof.

BACKGROUND OF THE INVENTION

Thrombin is a proteolytic enzyme having multiple functions in blood coagulation. Thrombin is formed from prothrombin (coagulation Factor II), a circulating zymogen precursor protein in the plasma. It is proteolytically cleaved to form thrombin in the coagulation cascade. Thrombin in turn acts as a serine protease that converts soluble fibrinogen into insoluble strands of fibrin, as well as catalyzing many other coagulation-related reactions.

Thrombin is widely used in clinical applications as a coagulation factor to staunch bleeding of wounds by conversion of fibrinogen to fibrin. It is a common component of surgical dressings, and has been used in combination with fibrinogen and other coagulation proteins in two-component hemostatic systems such as fibrin glues, adhesives, and sealants.

Thrombin powder for use in preparation of pharmaceutical compositions is commonly prepared by lyophilization of a solution.

The term "lyophilization" typically refers to the process of freezing a solution and then reducing the concentration of water e.g. by sublimation to levels which do not support biological or chemical reactions.

Lyophilization is a batch process which is limited by the capacity of the lyophilizer and usually lasts for several days. This puts the entire drying batch at risk for a significant amount of time until the process is completed. Furthermore, processing the resulting lyophilized "cake" into powder requires executing additional steps e.g. breaking, sieving and/or milling to further reduce particle size. These steps may decrease the potency and mass yield of the dry product. Advantageously, using a spray-drying process instead of lyophilization provides a cost effective, continuous and high-capacity process, in which the dry product is immediately obtained in a form of dry powder and not as a "cake".

As used herein, the term "cake" or "solid cake" refers to a porous and spongy structure-like composition resulting from the lyophilization process.

Spray drying involves atomization of a liquid, such as a solution, suspension or emulsion, for example by spraying through a spray nozzle while contacting with an atomizing gas to form spray particles; by two-fluid nozzle atomization, wherein spray is created by combination of a liquid flow and a gas flow, in which the atomization energy is provided by the gas flow; or by centrifugal atomization, wherein the solution is delivered in a rotating disk, such that spray is created by the energy created by the rotation of the disc. Alternatively, the liquid flow may be sprayed using a pressure nozzle in which the liquid flow is forced through a small aperture, the change in pressure transforming the liquid flow into spray of small droplets.

Formation of spray particles is followed by drying of the spray in a flow of a hot gas (e.g. air or nitrogen) provided by a drying gas conduit. The spray particles dry rapidly into powder, which is then separated from the hot airflow in a cyclone device, and may be collected in a container e.g. a vial. The spray drying process is controlled by several key process parameters, including drying air flow rate and temperature, atomizing air flow rate, solution flow rate and more.

Generally, enzymes such as thrombin are sensitive to the high temperatures and sheer stress conditions used in prior art spray drying processes, which usually cause denaturation and subsequent loss of potency of the enzyme. For example, thrombin in solution is sensitive to temperatures of about 45° C. or above.

The prior art solves this problem by using relatively low thrombin concentrations in the solution used for spray drying, or by increasing the concentration of carbohydrates, such as trehalose in the solution. These conditions result in a spray dried powder comprising a low concentration of thrombin (generally up to about 1 IU/mg).

Examples of background art spray drying processes for production of thrombin powder and uses thereof include U.S. Pat. No. 6,113,948; U.S. Publication No. 2012/0315305; PCT Publication No. WO 92/18164; U.S. Pat. No. 6,416,739; European Patent No. EP0713388B1; U.S. Pat. No. 8,846,105; U.S. Pat. No. 6,703,047; U.S Publication No. 20120121532; U.S. Publication No. 20100249044; PCT Publication No. WO 14/135689; J Microencapsul. 2013; 30(7):624-31. Doi: 10.3109/02652048.2013.770097. Epub Mar. 14 2013; Biotechnol Appl Biochem. 1995 October; 22 (Pt 2):203-14; and Excipient Mediated Biostabilization of Protein Using Spray Drying Technique—Thesis work done by Priyadarsini Pattnayak for a degree of master of technology, Biotechnology and medical engineering, under the guidance of Prof. Gyana Ranjan Satpathy, National institute of technology, Rourkela, India. September 2010.

SUMMARY OF THE INVENTION

The invention, in some embodiments thereof, relates to spray-dried thrombin powder comprising microcapsules, methods of preparation thereof and uses thereof.

The spray dried thrombin powder may be produced by controlling one or more of the following parameters: composition of the thrombin solution used for the spray-drying process, spray parameters (e.g. solution flow rate, atomizing gas flow rate), drying gas parameters (e.g. drying gas flow rate, drying gas temperature), and powder collection parameters (e.g. cooling gas flow).

It was surprisingly found that increasing the rate of a drying gas flow results in a reduction in the water content of the spray dried powder, without increasing the temperature used for the drying process.

It was further found that introduction of a cooling gas downstream of the drying column lowers the temperature of the dried particles below their glass transition temperature. The particles become less adhesive and more elastic in nature and therefore tend to adhere less to the inner walls of the spray dryer, leading to an increase in mass yield.

In some embodiments, the method comprises use of a specific aqueous thrombin composition which, in some embodiments, comprises relatively low concentrations of stabilizing protein carriers and carbohydrates e.g. sugars as compared to concentrations of such carriers and proteins known in the art. For example, U.S. Pat. No. 6,416,739 discloses use of 10-20 (% w/v) carrier protein, as compared to the range of 0.06 to about 6.0% (w/v) of carrier protein disclosed herein; while U.S. Pat. No. 8,846,105 discloses 20-30% (w/v) of sugar, as compared to the range of 0.2-5% (w/v) disclosed herein.

It was surprisingly found that use of the spray-drying methods and aqueous compositions described herein result in production of thrombin powders which have high levels of thrombin activity i.e. are highly concentrated (in some embodiments, having a thrombin content of from about 20 to about 30 IU/mg, such as about 24 IU/mg), are dry (in some embodiments, having less than 5% w/w water content), and have high density (in some embodiments, having a density of from about 0.1 to about 1.0 g/ml, such as about 0.46 g/ml thrombin), while retaining high thrombin activity (in some embodiments, above 90%).

In some embodiments, the relevant density is the conditioned bulk density. In some embodiments, the relevant density is the tapped density.

Aspects and embodiments of the invention are described in the specification hereinbelow and in the appended claims.

According to an aspect of some embodiments described herein, there is provided spray-dried thrombin powder comprising microcapsules, the powder comprising: thrombin, a carrier protein and a carbohydrate, wherein the ratio of thrombin (IU) to carrier protein (mg) is about 0.85:1 to 66,875:1, and wherein the ratio of thrombin (IU) to carbohydrate (mg) is 0.75:1 to 26,750:1.

In some embodiments, the microcapsules comprise: thrombin, a carrier protein and a carbohydrate, wherein the ratio of thrombin (IU) to carrier protein (mg) is about 0.85:1 to 66,875:1, and wherein the ratio of thrombin (IU) to carbohydrate (mg) is 0.75:1 to 26,750:1.

In some embodiments, the ratio of thrombin (IU) to carrier protein (mg) is from about 110:1 to about 285:1, optionally from about 129:1 to about 219:1.

In some embodiments, the ratio of thrombin (IU) to carbohydrate (mg) is from about 40:1 to about 64:1, optionally from about 35:1 to about 75:1.

In some embodiments, the carrier protein is selected from the group consisting of albumin, casein, keratin and a combination thereof.

In some embodiments, the carrier protein comprises albumin, optionally human serum albumin.

In some embodiments, the carrier protein is albumin, optionally human serum albumin.

In some embodiments, the carrier protein comprises casein. In some embodiments, the carrier protein is casein.

In some embodiments, the carrier protein comprises keratin. In some embodiments, the carrier protein is keratin.

In some embodiments, the carbohydrate is a sugar alcohol, optionally selected from the group consisting of glycerol, sorbitol, xylitol and mannitol. In some embodiments, the sugar alcohol comprises mannitol. In some embodiments, the sugar alcohol is mannitol.

In some embodiments, the carbohydrate is a saccharide, such as a saccharide selected from the group consisting of a monosaccharide, a disaccharide (optionally selected from the group consisting of sucrose, trehalose and a combination thereof), an oligosaccharide, a polysaccharide and a combination thereof.

In some embodiments, the powder comprises thrombin, albumin and mannitol, wherein the ratio of thrombin (IU) to albumin (mg) is from about 0.85:1 to 66,875:1, and wherein the ratio of thrombin (IU) to mannitol (mg) is from about 0.75:1 to about 26,750:1, optionally from about 35:1 to about 65:1, such as about 50:1.

In some embodiments, the ratio of thrombin (IU) to albumin (mg) is from about 100:1 to about 300:1, from about 110:1 to about 285:1, from about 120:1 to about 240:1, such as from about 129:1 to about 219:1. In some embodiments, the ratio of thrombin (IU) to albumin (mg) is about 160:1.

In some embodiments, the ratio of thrombin (IU) to mannitol (mg) is from about 35:1 to about 75:1, such as from about 40:1 to about 64:1.

In some embodiments, the spray-dried thrombin powder comprises thrombin at a concentration of from about 0.6 to about 535 IU/mg solids.

In some embodiments, the spray-dried thrombin powder comprises carbohydrate (such as mannitol) at a concentration of from about 0.02 to about 0.8 mg/mg solids.

In some embodiments, the spray-dried thrombin powder comprises carrier protein at a concentration of from about 0.008 to about 0.7 mg/mg solids.

In some embodiments, the spray-dried thrombin powder comprises albumin at a concentration of from about 0.008 to about 0.7 mg/mg solids.

In some embodiments, the spray-dried thrombin powder comprises thrombin at a concentration of from about 20 to about 40 IU/mg solids, albumin at a concentration of from about 0.1 to about 0.2 mg/mg solids, and mannitol at a concentration of from about 0.5 to about 0.6 mg/mg solids.

In some embodiments, the spray-dried thrombin powder comprises thrombin at a concentration of from about 22 to about 35 IU/mg solids, albumin at a concentration of from about 0.16 to about 0.17 mg/mg solids, and mannitol at a concentration of from about 0.55 to about 0.56 mg/mg solids.

In some embodiments, the spray-dried thrombin powder comprises thrombin, casein and mannitol, wherein the ratio of thrombin (IU) to casein (mg) is about 0.85:1 to 66,875:1, and wherein the ratio of thrombin (IU) to mannitol (mg) is 0.75:1 to 26,750:1.

In some embodiments, the spray-dried thrombin powder further comprises calcium at a concentration of from about 0.006 to about 0.115 mg/mg solids, optionally from about 0.034 to about 0.057 mg/mg solids, optionally from about 0.044 to about 0.048 mg/mg solids.

In some embodiments, a total salt concentration of the spray-dried thrombin powder is from about 0.1 to about 0.4 mg/mg solids, optionally from about 0.25 to about 0.30 mg/mg solids.

In some embodiments, the spray-dried thrombin powder further comprises sodium chloride at a concentration of from about 0.1 to about 0.3 mg/mg solids, optionally from about 0.19 to about 0.2 mg/mg solids.

In some embodiments, the spray-dried thrombin powder further comprises acetate at a concentration of from about 0.012 to about 0.086 mg/mg solids.

In some embodiments, the spray-dried thrombin powder comprises from about 0.001% to about 5% (w/w) thrombin.

In some embodiments, the spray-dried thrombin powder comprises less than about 5% water (w/w), such as less than about 4%, or less than about 3% water (w/w).

In some embodiments, the spray-dried thrombin powder has a particle size distribution of D50 of from about 5 to about 13 μm and D90 of from about 15 to about 25 μm.

In some embodiments, the powder density of the spray-dried thrombin powder is from about 0.1 to about 1.0 g/ml, optionally from about 0.4 to about 0.6 g/ml.

In some embodiments, the powder flowability of the spray-dried thrombin powder as measured by Freeman Technology FT4 Powder Rheometer (i.e. by moving a blade in upward lifting mode of displacement, using the Freeman Technology FT4 Powder Rheometer), is from about 5 to about 15 mJ/g, optionally from about 9 to about 10 mJ/g.

The resulting spray dried thrombin powder/microcapsules may be stored for a relatively long period of time. Following storage, the powder/microcapsules can be used as is or can be reconstituted by the addition of various volumes of an aqueous solution such as water for injection. The volume added during reconstitution can be similar to the volume of the solution before spray drying, lower or higher.

According to a further aspect of some embodiments described herein, there is provided an aqueous composition suitable for use in preparing thrombin microcapsules, the aqueous composition comprising: thrombin, a carrier protein and a carbohydrate, wherein the ratio of thrombin (IU) to carrier protein (mg) is about 1.6:1 to 5,000:1, and wherein the ratio of thrombin (IU) to carbohydrate (mg) is 2:1 to 1,500:1.

According to a further aspect of some embodiments described herein, there is provided a method for preparing thrombin microcapsules, the method comprising the steps of:

providing an aqueous composition comprising: thrombin, a carrier protein and a carbohydrate, wherein the ratio of thrombin (IU) to carrier protein (mg) is about 1.6:1 to 5000:1, and wherein the ratio of thrombin (IU) to carbohydrate (mg) is 2:1 to 1500:1; and spray drying the aqueous composition.

In some embodiments, spray drying comprises:

introducing the aqueous composition into a spray drying device;

producing droplets from the aqueous composition introduced into the device; and evaporating water from the droplets by a drying gas flow, thereby preparing thrombin microcapsules.

In some embodiments, producing droplets from the aqueous composition comprises using an atomizing gas flow.

In some embodiments, the ratio of the rate of introducing the aqueous composition into the spray drying device: rate of atomizing gas flow is at least 1:1000.

In some embodiments, evaporating water from the droplets comprises directing the droplets into the drying gas flow in a drying column at a temperature of from about 100 to about 170° C.

In some embodiments, the ratio of the rate of introducing the aqueous composition into the spray drying device to the rate of atomizing gas flow to the rate of drying gas flow is 1: (at least 1000):(at least 43,000).

In some embodiments, the currents of the aqueous composition flow, atomizing gas flow and drying gas flow are co-axial in the same direction.

In some embodiments, the method further comprises cooling the thrombin microcapsules by exposure to a cold gas flow.

In some embodiments, the rate of introducing the aqueous composition into the spray drying device is from about 100 to about 1000 ml/hr, optionally from about 200 to about 800 ml/hr, optionally from about 300 to about 500 ml/hr.

In some embodiments, the rate of atomizing gas flow is from about 3 to about 20 l/min, optionally from about 5 to about 15 l/min, optionally from about 7 to about 9 l/min.

In some embodiments, the rate of drying gas flow is from about 0.1 to about 1.0 m$^3$/min, optionally from about 0.3 to about 0.6 m$^3$/min.

In some embodiments, the aqueous composition comprises from about 100 to about 3000 IU/ml thrombin.

In some embodiments, the aqueous composition comprises from about 0.06 to about 6.0% (w/v) carrier protein.

In some embodiments, the aqueous composition comprises from about 0.2 to about 5% (w/v) carbohydrate.

In some embodiments of the method disclosed herein, the carbohydrate is a sugar alcohol, such as mannitol.

In some embodiments of the method disclosed herein, the carbohydrate is a saccharide, such as a saccharide selected from the group consisting of a monosaccharide, a disaccharide (optionally selected from the group consisting of sucrose, trehalose and a combination thereof), an oligosaccharide, a polysaccharide and a combination thereof.

In some embodiments of the method disclosed herein, the carrier protein is selected from the group consisting of albumin, casein, and keratin.

In some embodiments of the method disclosed herein, the carrier protein comprises albumin.

In some embodiments of the method disclosed herein, the carrier protein is albumin.

In some embodiments of the method disclosed herein, the carrier protein comprises casein.

In some embodiments of the method disclosed herein, the carrier protein is casein.

In some embodiments of the method disclosed herein, the carrier protein comprises keratin.

In some embodiments of the method disclosed herein, the carrier protein is keratin.

In some embodiments, the aqueous composition comprises calcium at a concentration of from about 5 mM to about 100 mM, optionally from about 30 to about 50 mM, optionally from about 38 to about 42 mM.

In some embodiments, the aqueous composition comprises acetate at a concentration of from about 7 to about 50 mM, optionally from about 15 to about 25 mM, from about 18 to about 20 mM.

In some embodiments, the aqueous composition comprises sodium chloride at a concentration of from about 100 to about 200 mM, optionally from about 114 to about 120 mM.

In some embodiments, the aqueous composition comprises:

from about 800 to about 1200 IU/ml thrombin;
from about 0.5 to about 0.65% (w/v) carrier protein;
from about 1.85 to about 2.05% (w/v) carbohydrate;
from about 38 to about 42 mM calcium;
from about 18.0 to about 20.0 mM acetate; and
about 60-240 mM sodium chloride, the aqueous composition having a density of from about 1.01 to about 1.03 g/ml.

In some embodiments, the composition having a density of from about 1.01 to about 1.03 g/ml.

In some embodiments, the aqueous composition comprises about 1000 IU/ml thrombin.

In some embodiments of the aqueous composition, the carrier protein comprises from about 0.06 to about 6.0% (w/v) albumin e.g. 0.6% (w/v).

In some embodiments of the aqueous composition, the carbohydrate comprises from about 0.2 to about 5% (w/v) mannitol e.g. about 2.0% (w/v) mannitol. In some embodiments, the pH range of the aqueous composition is from about 5 to about 8, such as from 6.9 to 7.1.

In some embodiment, the density range of the aqueous composition is from about 1.001-1.1 gr/ml.

In some embodiments, there is provided a spray-dried thrombin powder comprising microcapsules prepared according to any of the embodiments of the method disclosed herein.

In some embodiments, there is provided a matrix comprising the spray-dried thrombin powder according to any of the embodiments disclosed herein. In some such embodiments, the high density (e.g. from about 0.1 to about 1.0 g/cm³, optionally from about 0.4 to about 0.6 cm³) of spray-dried thrombin powder disclosed herein enables a smaller volume of powder to be used per cm² of matrix, as compared to lyophilized and milled thrombin powders, such that the powder height on the matrix is lower and thus adheres more easily to the matrix surface.

In some embodiments, the conditioned bulk density of the spray dried powder is about 0.46 g/cm³, and the tapped density of the spray dried powder is about 0.58 g/cm³.

In some embodiments, the matrix is a patch, optionally a biodegradable patch.

In some embodiments, the patch comprises a woven fabric.

In some embodiments, the patch comprises a non-woven fabric.

In some embodiments, the patch comprises a single layer.

In some embodiments, the patch is multi-layered, optionally comprising two, three or more layers.

In some embodiments, the patch comprises oxidized regenerated cellulose, optionally oxidized regenerated cellulose matrix and non-woven PG910 fibers.

In some embodiments, the patch comprises gelatin.

In some embodiments, the patch may be applied on a bleeding tissue e.g. a wound and is able to achieve a time to hemostasis (i.e. the time to full cessation of bleeding) of less than 3 minutes when using a pig spleen model.

In some embodiments, the patch comprises any of the embodiments disclosed in PCT Publication No. WO 2007/117237.

In some embodiments, the matrix further comprises a fibrinogen powder.

In some embodiments, the fibrinogen powder is prepared by freeze-drying/lyophilization. In some such embodiments, the resulting lyophilized cake may be milled.

In some embodiments, there is provided a kit comprising a container comprising the spray-dried thrombin powder according to any of the embodiments disclosed herein, as a first component.

In some embodiments, the kit further comprises a second component selected from the group consisting of fibrinogen, gelatin, collagen, Oxidized Regenerated Cellulose and a combination thereof.

In some embodiments, the second component is in a form selected from the group consisting of a powder, beads, granules, agglomerates.

In some embodiments, the second component is in a form selected from the group consisting of a solution, a paste, gel, and slurry.

In some embodiments, the fibrinogen is in powder form.

In some embodiments, the fibrinogen is a solution e.g. liquid or frozen form.

In some embodiments, the first component and the second component are provided together within the same container.

In some embodiments, the second component is provided within a separate container from the first component.

In some embodiments, the second component is in a form selected from the group consisting of a sponge, a pad, a patch, a bandage, and a gauze.

The spray-dried thrombin powder, matrix or kit as disclosed herein can be used for any therapeutic purpose. The term "any therapeutic purpose" refers to any curative or preventive treatment in a subject. Exemplary therapeutic purposes include, but are not limited to, sealing a bore hole formed in a tissue or organ e.g. a bone; anastomosis at blood vessels; joining tissue parts e.g. soft tissue parts; treating or preventing dura defects e.g. tears and leaks following dural injections, fissures or cracks; treating or preventing bleeding; treating or preventing air leaks such as following pulmonary lung resection; treating or preventing defects following intestinal perforation; treating or preventing defects following anastomosis procedure carried out in any tissue e.g. uterine, esophagus, stomach, pancreas, pancreatic duct, gall bladder, bile duct, intestinal (including the small intestine and the large intestine), and rectum; treating or preventing post-operation leaks in any tissue e.g. uterine, esophagus, stomach, pancreas, pancreatic duct, gall bladder, bile duct, intestinal (including the small intestine and the large intestine), and rectum; preventing or diminishing the occurrence of post-operative leaks at the staple or suture line e.g. by applying the kit components, patch or powder according to the invention onto at least a part of a defect such as a staple/suture line; for strongly affixing prosthesis e.g. during a hernia operation; for staple/suture line reinforcement; to prevent or diminish alveolar air leakage; treating or preventing renal defects; treating or preventing fistulas; treating or preventing heart defects e.g. penetrating heart wounds; reinforcing of a vascular graft prosthesis; and treating or preventing cerebrospinal fluid leakage.

In some embodiments, the spray-dried thrombin powder, kit or matrix according to any of the embodiments discloses herein is for use in providing hemostasis, sealing leaks and/or joining structures.

In some embodiments, there is provided a method of providing hemostasis, sealing leaks and/or joining structures in a subject in need thereof, the method comprising use of the spray-dried thrombin powder or the matrix according to any of the embodiments disclosed herein.

According to a further aspect of some embodiments described herein, there is provided an aqueous composition suitable for use in preparing thrombin microcapsules, the aqueous composition comprising: thrombin, a carrier protein and a carbohydrate, wherein the ratio of thrombin:carrier protein is about 1.6 IU:1 mg to 5,000 IU:1 mg, and wherein the ratio of thrombin:carbohydrate is 2 IU:1 mg to 1500 IU:1 mg.

According to a further aspect of some embodiments described herein, there is provided a method for preparing thrombin microcapsules, the method comprising the steps of: mixing thrombin, a carrier protein and a carbohydrate in an aqueous solution wherein the ratio of thrombin:carrier protein is about 1.6 IU:1 mg to 5000 IU:1 mg, and wherein the ratio of thrombin:carbohydrate is 2 IU:1 mg to 1500 IU:1 mg; and spray drying the aqueous solution.

Unless otherwise defined, all technical and scientific terms used herein have the same meaning as commonly understood by one of ordinary skill in the art to which the invention pertains. In addition, the descriptions, materials, methods, and examples are illustrative only and not intended to be limiting. Methods and materials similar or equivalent to those described herein can be used in the practices of the present invention.

As used herein, the term, "microcapsules" refers to particles having an outer shell and an inner volume, wherein the shape of the particles is substantially spherical or cylindrical and wherein a dimension of the outer shell is in the range of between 1 and 1000 micrometers, the particles comprising at least thrombin and/or at least one excipient. In embodiments wherein the particles are substantially spherical, the dimension is the diameter. In embodiments wherein the particles are substantially cylindrical, the dimension is the length.

The outer shell may be intact, burst, or collapsed.

The microcapsules disclosed herein are prepared by drying of liquid (e.g. aqueous thrombin composition) droplets comprising solutes.

Although solid microparticles may be produced from larger solid particles by micronization (typically by physical impact methods such as breaking, sieving, milling and/or grinding) such micronization method are not suitable for producing microcapsules. Hence, according to some embodiments, microcapsules are not prepared by micronization of larger particles.

As used herein, the term a "powder comprising microcapsules" is a powder that, in addition to microcapsules, also comprises other particles having diameters/length in the micrometer range and in the non-micrometer range, for example amorphous microcapsule debris (i.e, separate shell fragments, originating from a microcapsule that was burst or torn into separate shell fragments). In some embodiments, a "powder comprising microcapsules" according to the teachings herein is at least 50% by weight microcapsules, and in some embodiments, at least 55%, at least 60%, at least 65%, at least 70%, at least 75%, at least 80%, at least 85%, at least 90%, at least 95% or even 100% by weight microcapsules including any range between the disclosed percentages. In some embodiments, the outer shells of the microcapsules are intact.

In some embodiments, the "powder comprising microcapsules" comprises from about 50% to about 100% weight microcapsules, such as 50-55%, 50-60%, 50-65%, 50-70%, 50-75%, 50-80%, 50-85%, 50-90%, 50-95%, 50-99%, 55-60%, 55-65%, 55-70%, 55-75%, 55-80%, 55-85%, 55-90%, 55-95%, 55-99%, 60-65%, 60-70%, 60-75%, 60-80%, 60-85%, 60-90%, 60-95%, 60-99%, 65-70%, 65-75%, 65-80%, 65-85%, 65-90%, 65-95%, 65-99%, 70-75%, 70-80%, 70-85%, 70-90%, 70-95%, 70-99%, 75-80%, 75-85%, 75-90%, 75-95%, 75-99%, 80-85%, 80-90%, 80-95%, 80-99%, 85-90%, 85-95%, 85-99%, 90-95%, 90-99%, 95-99%, 90-100%, 95-100% by weight microcapsules.

In some embodiments, the "powder comprising microcapsules" comprises from about 90% to about 100% weight microcapsules.

As used herein, the term, "carrier protein" refers to a protein which interacts reversibly with thrombin in an aqueous solution, i.e. without affecting the thrombin activity or structure.

As used herein, the term "aqueous thrombin composition" or "an aqueous composition" refers to a liquid comprising thrombin and at least one additional excipient, wherein the liquid comprises at least 50% by weight water. In preferred embodiments, the solution comprises at least 95% by weight water and not more than 5% by weight of thrombin and other solids dissolved therein, and in even more preferred embodiments, at least 98% by weight water and not more than 2% by weight of thrombin and other solids dissolved therein.

As used herein, the term "yield" with regard to thrombin activity, is the percentage of biological activity of thrombin upon reconstitution of the powder as compared to the activity of thrombin in the liquid aqueous thrombin composition prior to spray drying. The terms "thrombin yield" and "thrombin activity recovery" are used interchangeably.

"Thrombin activity" and "thrombin biological activity" is meant to include thrombin mediated conversion of heterologous substrates, including proteins e.g. fibrinogen into fibrin, as well as the conversion of Factor VIII to Factor VIIIa, XI to XIa, XIII to XIIIa, and Factor V to Va. A "heterologous substrate" is a substrate, preferably a protein substrate, other than thrombin. In some embodiments, the thrombin activity refers to conversion of fibrinogen into fibrin.

As noted above, microcapsules used in implementing the teachings herein are made by spray drying an aqueous thrombin solution.

In some embodiments, spray-drying, droplets are formed by spraying an aqueous thrombin solution through an atomizing spray nozzle into a drying chamber called the "two-fluid nozzle atomization", and then evaporating the water from the droplets to form the desired microcapsules by a hot drying gas flow. Any suitable droplet size may be used to implement the teachings herein.

In some embodiments, droplets are formed by pressure nozzle atomization, wherein spray is created by forcing a solution through an opening.

In some embodiments, droplets are formed by centrifugal atomization, wherein spray is created by delivering the solution in a rotating disc. In some embodiments, the formed droplets have a diameter of equal to or lower than 1000 micrometer such as between 1 and 1000 micrometer.

As known in the art, droplets may be formed for spray drying by use of an atomizing gas, which may, for example, be provided at a temperature of about 15° C. to about 30° C. e.g. at room temperature (18-25° C.), that flows through the atomizing nozzle e.g. coaxially and in the same direction as the aqueous thrombin composition. Any suitable inert gas may be used as an atomizing gas including air, nitrogen and argon. Preferably, the atomizing gas is dry, containing as little water as possible, in some embodiments the atomizing gas has up to about 30% relative humidity.

As known in the art, droplets formed for spray drying may be sprayed into a drying gas inside the drying chamber and are carried away. Any suitable gas may be used as a drying gas at a temperature in the range of from about 100 to about 190° C., including air, nitrogen and argon. Preferably, the drying gas is dry, containing as little water as possible, such as having up to about 30% relative humidity. Typically, the drying gas is heated to an elevated temperature, as discussed in detail hereinbelow.

In some implementations of spray drying, the spray dried particles are recovered from the bottom of the drying chamber and transferred through a cooling chamber where the particles are cooled by contact with cold gas maintained at a temperature of from about 4 to about 24° C. Any suitable gas may be used as a cold gas including air, nitrogen and argon. Preferably, the cold gas is dry, containing as little water as possible, such as up to about 30% relative humidity. In some embodiments, the water content of the gas is about 0.0001%.

An example of a commercially available spray-drying apparatus 10 is illustrated in FIG. 1, comprising a drying column 12, having a spray nozzle 14 and a drying gas conduit 16.

Spray nozzle 14 has a proximal end 18 and a distal end 20, with a spray nozzle tip 22 at distal end 20.

A liquid conduit 24 is provided for carrying a liquid to be spray-dried to spray nozzle tip 22, through which the liquid is passed.

In some embodiments of the apparatus or method described herein, an atomizing component 25 is provided at distal end 20 of spray nozzle tip 22, and liquid conduit 24, having a distal end at spray nozzle tip 22, is provided for carrying a liquid to be spray dried to spray nozzle tip 22.

In some embodiments, the atomizing component 25 comprises an atomizing gas conduit 26, for guiding a flow of atomizing gas out through an atomizing gas outlet to contact liquid exiting the spray nozzle tip.

In some embodiments, the liquid is forced at high pressure through a small aperture located at the distal end of atomizing component 25, resulting in a pressure drop which turns the liquid into a spray of droplets e.g. fine droplets. Hence, in some embodiments, the atomizing component [25] comprises an aperture located at the distal end of said liquid conduit [24], wherein said liquid is forced out through said aperture to form a spray In some embodiments, atomizing component 25 comprises a rotating disc wherein the spray of the liquid is formed by centrifugal forces created by the rotation of the disc.

Drying gas conduit 16 comprises a drying-gas outlet 28 for providing a drying gas to dry the spray formed from the liquid upon exiting nozzle tip 22, thereby forming a powder.

The powder produced is separated from the drying gas by a cyclone unit 30, and is collected at the bottom of cyclone unit 30 e.g. in a collection container 32. The paths of the separated drying gas and of the powder are shown as 35 and 36, respectively.

In some embodiments, a cooling gas having lower temperature then drying gas (e.g. room temp or lower) is introduced downstream of drying column 12 by a cooling gas conduit 29.

In some embodiments, a method of preventing heat damage to the Thrombin is by preventing thrombin from overheating once in the liquid conduit 24 and nozzle tip 22 as shown in FIG. 2. FIG. 2 illustrates a prior art spray nozzle 14 including a heat exchange mechanism, comprising two tubes for circulating cool water i.e. a first tube 34*a* for entry of cool water, arranged concentrically around liquid conduit 24, and a second tube 34*b* for exit of cool water, with cool water circulating into first tube 34*a* and out of second tube 34*b* to a water bath, using a circulation pump (not shown).

As used herein, the term "atomizing gas" refers to a gas which flows in a parallel direction (co-current) to the flow of the liquid solution, forming low pressure which forms fine droplets from the liquid stream. In some embodiments, the atomizing gas is provided in an atomizer gas conduit 26 as shown in FIG. 1.

As used herein, the term "fine droplets" may refer to droplets which may be dried into powder upon contacting the drying gas flow under specific spray drying conditions, while large droplets may not be dried to powder under the same specific conditions, but instead stick to the inner walls of the spray drying apparatus, where they are dried, resulting in loss of process product i.e. reduction in mass yield. According to some embodiments, "fine droplets" are those having a diameter of equal to or lower than 1 mm. According to some embodiments, "large droplets" refer to droplets having a size of greater than 1 mm.

As used herein, the term "drying column" or "drying chamber" refers to a column in which the drying of the droplets takes place, implemented by a flow of drying gas at high temperature (such as from about 100 to about 170° C.). In some embodiments, a drying column or drying chamber is as shown as 12 in FIG. 1.

As used herein, the term "aqueous thrombin composition" refers to a solution which comprises thrombin and solutes.

As used herein, the term "drying gas" refers to a gas, which upon contact with the droplets, dries the droplets into a powder/microcapsules. In some embodiments, the drying gas is provided in conduit 16 and comprises drying-gas outlets 28 as shown in FIG. 1.

As used herein, the term "cold gas" refers to a gas which enters the spray dryer and merges with the drying gas flow in contact with the powder flow in order to reduce the temperature of the drying gas flow and of the powder. In some embodiments, the cold gas is provided in conduit 29 as shown in FIG. 1.

As used herein, the term "density" refers to the weight of solids per unit volume. The density can be measured in liquid, solid (e.g. powder) form and measured as g/ml or $g/cm^3$. For powder, the density can be "conditioned bulk density" or "tapped density".

Bulk density of a powder is the ratio of the mass of an untapped powder sample and its volume including the contribution of the interparticulate void volume.

As used herein, the term "conditioned bulk density" refers to the density of a bulk powder sample which has undergone a conditioning step, in which the powder is displaced (e.g. using a rotating blade) in order to loosen the powder to remove any pre compaction and/or excess air.

As used herein, the term "tapped density" refers to an increased bulk density attained after mechanically tapping a vessel (e.g. container) containing the powder sample.

Thrombin microcapsules formed by spray-drying can be used as a blood clotting agent. In some embodiments, the thrombin microcapsules are physically associated with (i.e. incorporated in or attached to) a matrix, that is to say, a solid object such as a patch of woven or non-woven fabric.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein the term "about" refers to ±10%.

Fibrinogen and thrombin can optionally be prepared from an initial blood composition. The blood composition can be whole blood or blood fractions, i.e. a fraction of whole blood such as plasma. The origin of the fibrinogen and thrombin can be autologous whereby they would be manufactured from the patient's own blood, from pooled blood or fractions. It is also possible that thrombin and fibrinogen are prepared by recombinant methods.

In one embodiment of the invention, the fibrinogen comprises a biologically active component (BAC) which is a solution of proteins derived from blood plasma, optionally further comprising anti fibrinolytic agents such as tranexamic acid and/or stabilizers such as arginine, lysine, pharmaceutically acceptable salts thereof, or mixtures thereof. BAC is optionally derived from cryoprecipitate, in particular concentrated cryoprecipitate.

The term "cryoprecipitate" refers to a blood component which is obtained from frozen plasma prepared from whole blood, recovered plasma or from source plasma which is collected by plasmapheresis. A cryoprecipitate is optionally obtained when frozen plasma is slowly thawed in the cold, typically at a temperature of 0-4° C., resulting in the formation of precipitate that contains fibrinogen and factor XIII. The precipitate can be collected, for example, by centrifugation and dissolved in a suitable buffer such as a buffer containing 120 mM sodium chloride, 10 mM trisodium citrate, 120 mM glycine, 95 mM arginine hydrochloride, 1 mM calcium chloride. The solution of BAC optionally comprises additional factors such as for example factor VIII, fibronectin, von Willebrand factor (vWF), vitronectin, etc. for example as described in U.S. Pat. No. 6,121,232 and WO9833533. The composition of BAC optionally comprises stabilizers such as tranexamic acid and arginine hydrochloride. The amount of tranexamic acid in the solution of BAC is optionally in the range of from about 80 to about 110 mg/ml. The amount of arginine hydrochloride is optionally in the range of from about 15 to about 25 mg/ml.

Optionally, the fibrinogen solution is buffered to a physiological compatible pH value. The buffer comprises glycine, sodium citrate, sodium chloride, calcium chloride and water for injection as a vehicle. Glycine is optionally present in the composition at a concentration in the range of from about 6 to about 10 mg/ml; sodium citrate is optionally present at a concentration in the range of from about 1 to about 5 mg/ml; sodium chloride is optionally present at a concentration in the range of from about 5 to about 9 mg/ml; and calcium chloride is optionally present at a concentration in the range of from about 0.1 to about 0.2 mg/ml.

In one embodiment of the invention, the fibrinogen is derived from blood e.g. BAC composition. In another embodiment of the invention, the concentration of plasminogen and/or plasmin in the blood derived component is lowered. The removal of plasmin and plasminogen from the blood derived component can be carried out as described in U.S. Pat. No. 7,125,569 and WO02095019.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1:
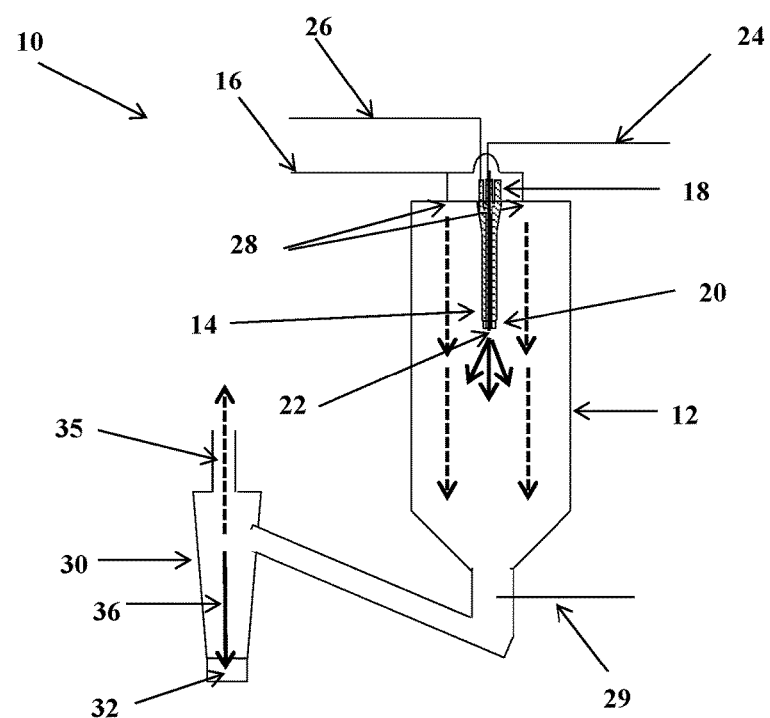
FIG. 1 (Prior Art) is a schematic representation of a spray-drying apparatus.
Figure 2:
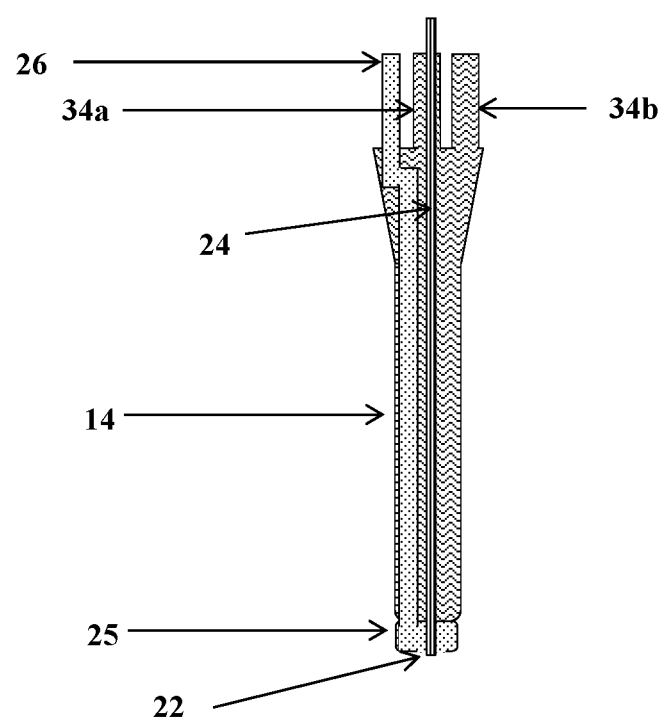
FIG. 2 (Prior Art) is a schematic representation of a spray nozzle.

The invention, in some embodiments thereof, relates to spray-dried thrombin powder comprising microcapsules, methods of preparation thereof and uses thereof.

The principles, uses and implementations of the teachings herein may be better understood with reference to the accompanying description. Upon perusal of the description, one skilled in the art is able to implement the invention without undue effort or experimentation.

Before explaining at least one embodiment in detail, it is to be understood that the invention is not necessarily limited in its application to the details of construction and the arrangement of the components and/or methods set forth in the following description. The invention is capable of other embodiments or of being practiced or carried out in various ways. The phraseology and terminology employed herein are for descriptive purpose and should not be regarded as limiting.

As demonstrated in the Results section below (see Examples 1, 2 and FIG. 3), embodiments of reconstituted thrombin compositions disclosed herein that include both salts and a carrier protein have a relatively high thrombin activity-recovery (~80%, composition 6). Post spray drying thrombin activity-recovery is higher for reconstituted thrombin compositions which further included a carbohydrate, especially a sugar alcohol such as mannitol, (~85%, composition 7), and even higher when the reconstituted thrombin composition further includes a relatively large amount of calcium chloride, (~95%, composition 8). All things being equal, higher thrombin activity-recovery is achieved with compositions having a relatively high carrier protein/thrombin ratio (see Tables 2B and 3).

As demonstrated in the Results section below, embodiments of reconstituted thrombin compositions disclosed herein that include both a carrier-protein (e.g., albumin) and a carbohydrate (e.g., a sugar alcohol such as mannitol) have exceptionally high thrombin activity-recovery (see Examples 2 and 4), surprisingly even at high thrombin concentrations (see Examples 6 and 6). Without wishing to be held to any one theory, it is currently believed that the combination of carrier protein and carbohydrate helps maintain thrombin structure and potency, inter alia, by providing heat protection.

The thrombin activity recovery provided by embodiments of the teachings herein is superior to that provided by prior art. For example, US Patent Application Publication No. 2012/0315305 discloses spray-dried thrombin having a concentration of 25 to 1000 IU/g. The comparable Example 6 shows that a thrombin composition according to the teachings herein that includes a carrier protein provides a substantially higher thrombin activity recovery.

It is believed that some of the advantages of some of the embodiments according to the teachings herein are a result of the spray-drying conditions used that lead to production of active thrombin powder at high mass and potency yields and at high concentrations. In some embodiments, a high level of thrombin activity recovery is achieved by at least one of:

drying gas (e.g., dry air or nitrogen) at a temperature no higher than 190° C.; a ratio of thrombin solution flow rate:atomizing gas flow rate of at least 1:1000. i.e. when spray-drying 1 ml of thrombin solution per minute, atomizing gas flow rate is preferably at least 1 l/min.

a ratio of thrombin solution flow rate:drying gas flow rate of at least 1:43,000. i.e. when drying 1 ml of thrombin per minute, the drying gas flow rate is preferably at least 43 l/min.

Specifically, in Example 8a drying gas temperature of 190° C. yielded spray-dried thrombin powder with water content as low as 1.5%. In Example 9 is seen that to obtain spray-dried thrombin powder with a high thrombin activity recovery and low water content, it is preferable to set the inlet gas temperature to no more than about 170° C. In some embodiments, to reduce water content while maintaining thrombin activity recovery, drying gas flow rate is increased rather than drying gas temperature.

It has surprisingly been found that in some embodiments increasing the drying gas flow rate leads to a decrease in the water content in the resulting dry thrombin composition despite the reduced retention time of the thrombin in the drying column.

It is considered that increased drying gas flow rate would decrease the pressure over the drying particles, resulting in an increase in evaporation. Without wishing to be held to any one theory, it is noticed that when the powder reaches the bottom of the drying column, it is hot and particles would tend to adhere to the inner parts of the drying column and the tubes that deliver the powder flow from the drying column to the cyclone, resulting in reduced mass yield. This adhesion would be expected to occur when the powder is at a temperature greater than its glass transition temperature, which causes the surface of the particles to be 'rubbery' or plastic in nature. Introducing cool gas into the bottom of the drying column would therefore be expected to reduce the temperature at which the particles flow, thus reducing surface temperature of the particles below their glass transition temperature, such that the particles would be present in a glassy or elastic state and preventing them from adhering to the inner parts of the system, such that mass yield is consequently increased.

As shown in Example 7, embodiments with particularly low drying gas temperature (140° C.) and high drying gas flow rate (thrombin solution: drying gas flow rate 1:900000) provided a spray-dried thrombin powder that was dry, had a narrow particle size distribution, and had a high thrombin activity recovery.

Embodiments of spray-dried thrombin compositions according to the teachings herein having a relatively high thrombin concentration provide a number of advantages. For example, when a fibrin patch comprising such compositions is used, there is a higher thrombin concentration in the formed fibrin clot formed, resulting in more fibrin fibers in the clot, leading to greater clot strength and adhesion to tissue (see Example 10), as well as faster clot formation (Time To Hemostasis (TTH)<3 minutes, see Example 11).

Embodiments of spray-dried thrombin compositions according to the teachings herein can be stored at room temperature for extended periods of time without needing storage in a cool (i.e., 2-8° C.) or freezing (i.e. less than −18° C.).

The flowability of spray dried thrombin compositions according to the teachings herein are shown in Example 12. As used herein, the term "powder flowability" refers to the ease with which a powder will flow under a specified set of conditions, as measured with a powder rheometer (FT4 powder rheometer, Freeman technology, Gloucestershire, UK), by moving a blade in upward lifting mode of displacement. Examples of such conditions include the pressure on the powder, the roughness of the particle surface, the humidity of the air around the powder and the equipment the powder is flowing through or from. The flowability is expressed as the energy required to displace the powder composition, divided by the displaced powder weight. The demonstrated low specific energy of the composition means that less energy is required to displace the composition. Practically, during a manufacturing process, a low specific energy composition is less likely to cause interlocking and friction which may clog machinery (e.g., an auger dozer) used to transfer the composition.

Additionally, drying of embodiments of aqueous thrombin composition feed according to the teachings herein using embodiments of spray-drying processes according to the teachings herein for preparing spray-dried thrombin microcapsule compositions results in the production of highly concentrated thrombin compositions having dense particles. As shown in Table 17 (Example 12), the conditioned bulk density (i.e. the powder density wherein air gaps between the particles are not eliminated, for instance by tapping) of the spray-dried thrombin composition according to an embodiment of the teachings herein was 0.46 g/ml and the tapped density (the powder density after elimination of air gaps between the particles e.g. by tapping) was 0.58 g/ml, compared to conditioned bulk density of 0.37 g/ml and tapped density of 0.48 gr/ml for a comparable lyophilized composition.

EXAMPLES

Materials and Methods
Materials

Thrombin (NDC No. 63713-460, Manufactured by Omrix Biopharmaceuticals Ltd., Israel). In the experiments below, a thrombin component as in EVICEL® Fibrin Sealant (Manufactured by Omrix Biopharmaceuticals Ltd., Israel) was used.

Human Serum Albumin (Plasbumin 25, 25% sterile solution of albumin in aqueous diluent, NDC no. 13533-692-20) was acquired from Grifols USA, Research Triangle Park, N.C., USA.

D-Mannitol (Cat. No. 443907), Sodium Acetate Trihydrate (Cat. No. 1370121000), Calcium Chloride Dihydrate (1371015000) were obtained from Merck Milipore (Billerica, Mass., USA).

Until use, thrombin was stored in a standard laboratory freezer set to maintain a temperature of about −18° C., Human Serum Albumin and all solid materials were stored at room temperature (about 24° C.) not exceeding 30° C.

Equipment

Spray dryer. 4M8-TriX spray dryer was used (by ProCepT nv, Zelzate, Belgium).

Methods
Preparation of Thrombin Solution:

For each experiment, a desired amount of frozen thrombin solution (Omrix Biopharmaceuticals, Israel) was allowed to warm to room temperature inside a sealed bottle. A thrombin solution was made by dissolving the warmed thrombin in triple-distilled water at the desired concentration (see tables, below).

Spray Drying:

The prepared thrombin solution was drawn into a syringe and placed inside the syringe pump of the spray dryer. The syringe pump was set to the desired flow rate with feed valve closed.

While the syringe pump feed valve was closed, the spray dryer was activated and the desired atomizing gas flow rate, drying gas flow rate, drying gas temperature, cooling gas flow rate and cyclone gas flow rate were set.

The cooling gas flow rate and temperature were selected such as not to disrupt laminar flow in the drying column, but to reduce the gas flow temperature to below the glass transition temperature of the composition in order to prevent powder from sticking to the glass parts.

The spray dryer was allowed to run until a steady state was reached where the actually measured value of the parameters reached the set levels and remained steady. The feed valve was then opened, allowing the thrombin solution to flow through the feed inlet to the spray nozzle to be atomized by the atomizing gas flow to small droplets which then dried in the drying column. Spray dried thrombin powder was formed, which was collected in the powder outlet of the cyclone of the spray dryer.

The spray dried thrombin powder recovered from the cyclone was weighed in a de-humidifier at a relative humidity of below 30% and divided into samples of between 100-200 mg. Each sample was individually sealed in a test tube with a plug and sealed with Parafilm® (Bemis, Oshkosh, Wis., USA) until evaluation.

Characterization of the Spray-Dried Thrombin Powder

The spray-dried thrombin powder was characterized by determining the thrombin activity including thrombin activity recovery (compared to thrombin activity prior to spray drying), water content, particle size distribution, total and clotable protein, density (conditioned bulk and tapped), flowability and mass yield.

Thrombin Activity Determination

Thrombin activity of an aqueous thrombin solution was determined using a clotting time assay by measuring thrombin clotting activity in the solution according to the modified European Pharmacopeia Assay (0903/1997) procedure. Briefly, a calibration curve of thrombin concentration vs. clotting time was prepared by mixing a thrombin standard (Fibri-Prest® 2 by Beijing Stago Diagnosis Trading Co. Ltd, Beijing, China) with a 0.1% fibrinogen solution (Omrix Biopharmaceuticals Ltd., Israel) at various different thrombin concentrations (4, 6, 8, and 10 IU/ml), and measuring the time taken for each sample to clot using a clotting measurement device (STart® by Beijing Stago Diagnosis Trading Co. Ltd., Beijing, China).

For each analysis, a sample of approximately 35 mg spray-dried thrombin was dissolved in 1 ml double distilled water (to give a thrombin solution having thrombin activity of ~1000 IU/ml). This solution was diluted 1:200 to produce a solution having a potency of ~5 IU/ml). 40 µl of the diluted thrombin solution was mixed with 160 µl of 0.1% fibrinogen solution in the clotting measurement device. The clotting time of the sample was determined and the thrombin activity was extrapolated with reference to the calibration curve.

Water Content Determination

Water content determination was carried out using the volumetric Karl Fischer Titration method (KFT), which is based on the US Pharmacopoeia assay (USP 27, <921>, P. 2398-2399). Prior to the titration, the water was extracted from the spray-dried thrombin powder by adding about 10 ml dried methanol to about 100 to about 200 mg of the spray dried thrombin powder.

Particle Size Distribution Determination

The size distribution of particles suspended in liquid is measured by using the principles of light scattering. Measurement were carried out by using the particle size analyzer LS 13 320 (Beckman Coulter Inc., Pasadena, Calif., USA). The pattern measured by the LS 13 320 is the sum of the patterns scattered by each constituent particle in the sample. The LS 13 320 consists of an optical bench and Micro Liquid Module (MLM) which includes a chemically resistant liquid cell and stir bar to keep the suspended particles homogenously mixed. The system is designed to work with small quantities of suspension fluid (12 ml). A powder sample of between 100 and 200 mg of a spray-dried thrombin was suspended in 10 ml hydrofluoroether (HFE-7000, manufactured by 3M Company, Two Harbors, Minn., USA). The sample was placed in a micro-liquid module (MLM) and the particle size distribution was determined.

Total Protein and Clottable Protein

A total protein test was used to determine the total amount of proteins in a fibrin sealant patch sample. Powder is extracted from a fibrin sealant patch and dissolved in a solubilizing solution which is capable of dissolving the proteins in the sample. The protein concentration is determined by the Lowry method against a calibration curve.

Friability

The friability of patches comprising fibrinogen and thrombin powders was intended to determine the degree of powder flaking or crumbling from a fibrin sealant patch after a force was applied to a sample of the patch. To measure the friability, a patch was cut to a specific size, and the weight of the sample was determined. The sample was subjected to a defined impact force by placing the sample within a vial and dropping the vial through a tube of fixed height onto a rubber stopper. The amount of powder loss was determined by weighing the patch sample and the percentage of weight reduction of the sample was calculated.

Tissue Peel

The adhesion strength of a fibrin sealant patch to calf corium tissue substrate was determined by using the 5000 Series Instron Tensiometer, Instron Corp. Norwood, Mass., USA). To measure the adhesion strength, a fibrin patch was applied to the surface of the corium and wetted with saline. The average force necessary to subsequently perform a 90 degree peel test of the fibrin patch from the calf corium tissue was determined by measuring the integral under the force vs distance curve.

Tensile Strength

The tensile strength of a dogbone-shaped fibrin patch sample having width on the sides of 25 mm, width in the middle of 15 mm and length 102 mm was determined. The sample was placed between Instron grips (5000 Series Instron Tensiometer, Instron Corp. Norwood, Mass., USA). The crosshead was moved at a pre-determined constant rate of extension of 305 mm/min. The test was concluded when a peak load drop of 30% was achieved, indicating a rupture occurrence.

Density (Conditioned Bulk, Tapped)

Conditioned bulk density, tapped density and specific energy were measured using a powder rheometer (FT4 powder rheometer, Freeman technology, Gloucestershire, UK). Tests were carried out in a 25 mm vessel with a 23.5 mm blade at 250 taps.

The term "density" refers to the weight of solids per unit volume. The density can be measured in liquid, solid (e.g. powder) or gas form. For powder, the density can be "conditioned bulk density" or "tapped density". The bulk density of a powder is the ratio of the mass of an untapped powder sample and its volume including the contribution of the interparticulate void volume.

As used herein, the term "bulk density" refers to the density of a bulk powder sample of a known weight in a known volume size.

As used herein, the term "conditioned bulk density" refers to the density of a bulk, powder sample, which has undergone a conditioning step, in which the powder is gently displaced using a rotating blade in order to loosen the powder to remove any pre compaction or excess air.

As used herein, the term "tapped density" refers to the conditioned bulk density powder sample is tapped a constant number of times after which the density is measure.

Flowability (Specific Energy)

The FT4 powder rheometer (FT4 powder rheometer, Freeman technology, Gloucestershire, UK) was used to measure the resistance that the powder exerts on the rheometer blade (the resistance of the powder to flow), expressed as torque (radial resistance) and force (vertical resistance).

Specific energy (flowability)=[distance×(torque+force)]/split mass wherein distance refers to the distance travelled by the blade in an upward lifting mode of displacement.

As used herein, the term "split mass" refers to the mass of powder that was displaced during the measurement.

In the examples described below the test conditions were as follow: −5° helix and 100 mm/sec blade tip speed. A sample volume of 25 ml was used.

Example 1: Effect of Thrombin Solution Composition on Maintaining Thrombin Activity During Spray Drying Various thrombin solutions were prepared (including different salts and/or carbohydrates and/or proteins) in order to test the effect of the excipient(s) in solution on maintaining the thrombin activity during spray-drying.
Eight different such thrombin solutions were prepared as shown in Table 1:

TABLE 1

| Composition # | Thrombin [IU/ml] | Sodium Acetate [mM] | Sodium Chloride [mM] | Calcium Chloride [mM] | D(—) Mannitol [mg/ml] | HSA (human serum albumin) [mg/ml] |
|---|---|---|---|---|---|---|
| 1 | 1000 | 7 | 67 | 3 | — | — |
| 2 | 1000 | 7 | 67 | 40 | — | — |
| 3 | 1000 | 20 | 200 | 40 | — | — |
| 4 | 800 | 7 | 67 | 3 | 20 | — |
| 5 | 1200 | 7 | 67 | 3 | 20 | — |
| 6 | 1000 | 7 | 67 | 3 | — | 6 |
| 7 | 1000 | 20 | 200 | 3 | 20 | 6 |
| 8 | 1000 | 20 | 20 | 40 | 20 | 6 |

Compositions 1-8 were spray-dried as described above with the following parameters:
1. Thrombin sample flow rate: 400 ml/h;
2. Atomizing gas flow rate: 7 l/min;
3. Drying gas (dry air) flow rate: 600 l/min;
4. Drying gas (dry air) temperature: 140° C.;
5. Cooling gas (dry air) flow rate: 100 l/min;
6. Cyclone gas (dry air) flow rate: 150 l/min.

After recovery from the cyclone, each spray-dried thrombin composition (dried thrombin with excipients) was reconstituted in water to the same concentration as the parent solution. The thrombin activity of each reconstituted solution was compared to that of the respective parent solution. The relative activities are presented in the graph of FIG. 3.

Figure 3:
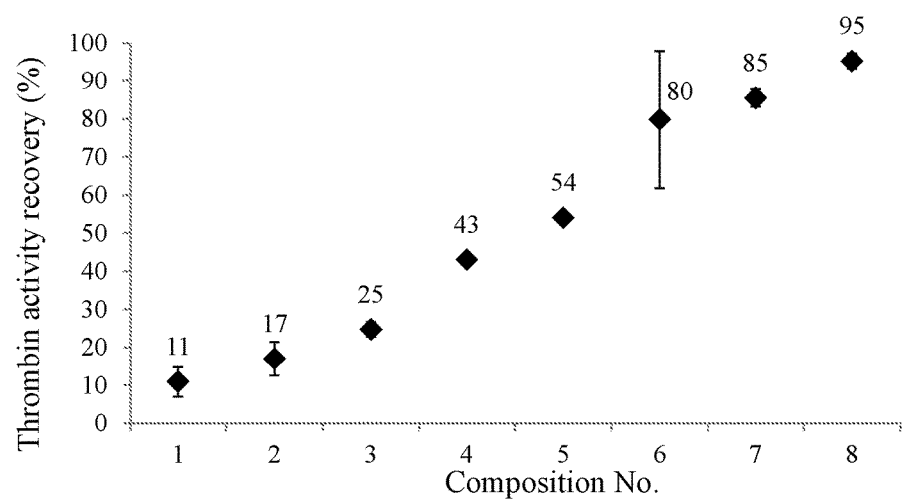
FIG. 3 is a plot showing the influence of thrombin solution composition on thrombin activity recovery (%) of spray dried thrombin powder.

As shown in FIG. 3, reconstituted compositions including salts alone (compositions 1-3) had a relatively low post spray-drying thrombin activity recovery (up to 25%). Reconstituted compositions with salts and a sugar alcohol (e.g., mannitol) had a modest post spray-drying thrombin activity recovery (~50%, compositions 4, 5). Reconstituted compositions with salts and a protein (e.g., human serum albumin, HSA) had a relatively high post spray-drying thrombin activity recovery (~80%, composition 6). Reconstituted compositions with salts, a sugar alcohol (e.g., mannitol) and a protein (e.g., human serum albumin, HSA) had a very high post spray-drying thrombin activity recovery (~85%, composition 7) that was even higher when the thrombin composition comprised salts, sugar alcohol and protein with a relatively large amount of calcium chloride, (thrombin activity recovery of ~95%, composition 8).

Example 2: Effect of Thrombin and Human Serum Albumin (Carrier Protein) Concentration on Maintaining Thrombin Activity During Spray Drying of Thrombin Solutions Fifteen thrombin solutions having different concentrations of thrombin and albumin, serving as a carrier protein, were prepared as shown in Table 2:

TABLE 2

| Composition # | Thrombin [IU/ml] | Human Serum Albumin [mg/ml] | Thrombin Activity Recovery (%) |
|---|---|---|---|
| 9 | 100 | 0.06 | 55-77 |
| 10 | 100 | 0.6 | 91-100 |
| 11 | 100 | 1.8 | 79-100 |
| 12 | 100 | 2.25 | 52-98 |
| 13 | 100 | 6.0 | 100 |
| 14 | 1000 | 0.006 | 23-55 |
| 15 | 1000 | 0.06 | 31-69 |
| 16 | 1000 | 0.6 | 62-98 |
| 17 | 1000 | 1.8 | 92-94 |
| 18 | 1000 | 2.25 | 81-83 |
| 19 | 1000 | 6.0 | 86-100 |
| 20 | 3000 | 0.06 | 67-75 |
| 21 | 3000 | 0.6 | 94-96 |
| 22 | 3000 | 1.8 | 58-62 |
| 23 | 3000 | 2.25 | 77-81 |

Compositions 9-23 were spray dried as described above. As discussed above, after spray drying, three 35 mg samples of each spray-dried thrombin composition were reconstituted in water to the same concentration as the parent solution. The thrombin activity of each reconstituted solution was measured twice and compared to that of the respective parent solution, giving a total of 6 measurements for each solution. The average thrombin activity recoveries are presented in Table 2.

An additional parameter was calculated which shows the ratio of albumin weight to thrombin activity in the parent solution and its effect on thrombin activity recovery post spray drying, as can be seen in Table 2b (sorted from low to high according to Albumin/thrombin (g/IU) ratio). Thrombin activity recovery shown represents average±standard deviation.

TABLE 2b

| Composition # | Albumin/thrombin (g/IU) | Thrombin Activity Recovery (%) |
|---|---|---|
| 14 | 0.006 | 23-55 |
| 20 | 0.02 | 67-75 |
| 15 | 0.06 | 31-69 |
| 21 | 0.2 | 94-96 |
| 9 | 0.6 | 55-77 |
| 16 | 0.6 | 62-98 |
| 22 | 0.6 | 58-62 |
| 23 | 0.75 | 77-81 |
| 17 | 1.8 | 92-94 |
| 18 | 2.25 | 81-83 |
| 10 | 6 | 91-100 |
| 19 | 6 | 86-100 |
| 11 | 18 | 79-100 |
| 12 | 22.5 | 52-98 |
| 13 | 60 | 100 |

The results indicate that the highest thrombin activity recoveries are achieved in compositions having relatively high albumin to thrombin levels (Table 2b) with only composition 21 as an outlier. However, having high ratio of albumin to thrombin does not guarantee high thrombin activity recovery post spray drying as can be seen by the large thrombin activity recovery variation obtained for compositions 11 and 12 and the relatively low thrombin activity recovery of compositions 22 and 23.

Example 3: Effect of Casein (Carrier Protein) Concentration on Maintaining Thrombin Activity During Spray Drying Four compositions of thrombin solution having different casein (carrier protein) concentrations were prepared as shown in Table 3:

TABLE 3

| Composition # | Thrombin [IU/ml] | Casein [mg/ml] | Thrombin Activity Recovery (%) |
|---|---|---|---|
| 24 | 1000 | 0.06 | 44-54 |
| 25 | 1000 | 0.6 | 60-76 |
| 26 | 1000 | 1.8 | 92-98 |
| 27 | 1000 | 6.0 | 78-100 |

Solutions 24-27 were spray dried as described above. As discussed above, after spray drying, three 35 mg samples of each spray-dried thrombin composition were reconstituted in water to the same concentration as the parent solution. The thrombin activity of each reconstituted solution was measured twice and compared to that of the respective parent solution, giving a total of 6 measurements for each solution. The thrombin activity recoveries obtained are presented in Table 3. The results achieved with casein are similar to the results achieved with albumin, meaning high thrombin activity recovery is obtained when ratio of carrier protein to thrombin is high however this does not guarantee high thrombin activity recovery as can be seen in high variance of the thrombin activity recovery in composition 27.

Example 4: Effect of Carbohydrate Type and Concentration on Maintaining Thrombin Activity During Spray Drying Twenty-five thrombin solutions having different Thrombin concentrations, carbohydrate types and carbohydrate concentrations, with or without a carrier protein were prepared, as shown in Tables 4 to 8:

TABLE 4

| Composition # | Thrombin (IU/ml) | Mannitol [mg/ml] | Thrombin Activity Recovery (%) |
|---|---|---|---|
| 28 | 800 | 2.0 | 43 |
| 29 | 1200 | 2.0 | 54 |
| 30 | 2000 | 2.0 | 49 |
| 31 | 3300 | 2.0 | 42 |

TABLE 5

| Composition # | Thrombin (IU/ml) | Trehalose [mg/ml] | Albumin [mg/ml] | Thrombin Activity Recovery (%) |
|---|---|---|---|---|
| 32 | 200 | 20 | — | 34-48 |
| 33 | 400 | 20 | — | 40-44 |
| 34 | 454 | 20 | — | 54-64 |
| 35 | 600 | 20 | — | 43-47 |
| 36 | 800 | 20 | — | 38-44 |
| 37 | 1000 | 20 | — | 57-63 |
| 38 | 454 | 20 | 0.6 | 76-86 |

TABLE 6

| Composition # | Thrombin (IU/ml) | Sucrose [mg/ml] | Albumin [mg/ml] | Thrombin Activity Recovery (%) |
|---|---|---|---|---|
| 39 | 1000 | 0.2 | — | 45 |
| 40 | 1000 | 2.0 | — | 71-75 |
| 41 | 1000 | 20 | — | 66-80 |
| 42 | 1000 | 0.2 | 0.6 | 54-64 |
| 43 | 1000 | 2.0 | 0.6 | 93 |
| 44 | 1000 | 20 | 0.6 | 81-93 |

TABLE 7

| Composition # | Thrombin (IU/ml) | Starch [mg/ml] | Thrombin Activity Recovery (%) |
|---|---|---|---|
| 45 | 1000 | 0.06 | 44-48 |
| 46 | 1000 | 0.6 | 36-46 |
| 47 | 1000 | 1.8 | 51-85 |
| 48 | 1000 | 6.0 | 57-81 |

TABLE 8

| Composition # | Thrombin (IU/ml) | Maltodextrin [mg/ml] | Thrombin Activity Recovery (%) |
|---|---|---|---|
| 49 | 1000 | 0.06 | 37-49 |
| 50 | 1000 | 0.6 | 48-56 |
| 51 | 1000 | 1.8 | 71-77 |
| 52 | 1000 | 6.0 | 59-89 |

Compositions 28-52 were spray dried. Samples were recovered and reconstituted in water as described above, and the thrombin activity of each reconstituted solution was compared to that of the respective parent solution. The relative activities are presented in the respective Tables 4-8.

The results show:

Table 4: addition of a sugar alcohol (mannitol) alone to the thrombin solution was not sufficient to maintain thrombin activity during spray drying.

Tables 5 and 6: addition of a disaccharide (trehalose in Table 5, sucrose in Table 6) alone to the thrombin solution was not sufficient to maintain thrombin activity during spray drying. However, when the disaccharide was added together with a carrier protein (albumin) there was substantial increase in thrombin activity recovery.

Tables 7 and 8: addition of a polysaccharide (starch in Table 7, maltodextrin in Table 8) alone to the thrombin solution was not sufficient to maintain thrombin activity during spray drying.

Example 5: Effect of Thrombin Concentration with Fixed Molar Ratio of Thrombin to Human Serum Albumin (Carrier Protein) on Maintaining Thrombin Activity During Spray Drying Three thrombin compositions having different thrombin and albumin concentrations were prepared, as shown in Table 9, wherein the molar ratio of thrombin to albumin was 1:6.4 in all three solutions:

TABLE 9

| Composition # | Thrombin (IU/ml) | Albumin (wt %) | Thrombin Activity Recovery (%) |
|---|---|---|---|
| 53 | 100 | 0.06 | 55-77 |
| 54 | 1000 | 0.6 | 62-98 |
| 55 | 3000 | 1.8 | 58-62 |

Samples of compositions 53-55 were spray dried. Samples were recovered and reconstituted in water as described above, and the thrombin activity of each reconstituted solution was compared to that of the respective parent solution. The thrombin activity recoveries are presented in Table 9. It is seen that the thrombin activities of the three reconstituted solutions was roughly the same, either low thrombin activity recovery (compositions 53 and 55) or high variance of thrombin activity recovery (composition 54).

Example 6: Effect of Trehalose (Disaccharide) on Maintaining Thrombin Activity During Spray Drying US Patent Application Publication No. 2012/0315305 discloses spray drying of a thrombin composition comprising trehalose and reports 97% thrombin activity recovery.

Solutions 56 and 57, similar to those described in US 2012/0315305 (except that the source of the thrombin was different and the spray dryer was of a different type), were prepared, as shown in Table 10. Additionally, a novel thrombin solution 58 including trehalose and a protein (human serum albumin) was prepared.

TABLE 10

| Composition # | Thrombin (IU/ml) | Trehalose (mg/ml) | CaCl₂ (mM) | Albumin (wt %) | Thrombin Activity Recovery (%) |
|---|---|---|---|---|---|
| 56 | 454 | 307 | 40 | — | 54-64 |
| 57 | 200 | 200 | — | — | 34-48 |
| 58 | 200 | 200 | — | 0.6 | 76-86 |

Compositions 56-58 were spray dried in similar spray drying conditions according to the publication. Samples were recovered and reconstituted in water, and the thrombin activity of each reconstituted solution was compared to that of the respective parent solution. The thrombin activity recoveries are presented in Table 10.

The results indicate that contrary to that reported in US 2012/0315305, solutions 56 and 57 showed a thrombin activity recovery of less than 65%. However, the addition of a carrier protein (human serum albumin) in composition 58 in accordance with some embodiments of the teachings herein led to a substantial increase in thrombin activity recovery.

Example 7: Spray Drying Process and Product Characterization of a Preferred Thrombin Composition Three liters of a composition 59, based on composition 8 of example 1, consisting of thrombin, albumin, mannitol, acetate, calcium and sodium chloride in water as shown in Table 11 were prepared.

TABLE 11

| Ingredient | Concentration | Presumed Role in Composition |
|---|---|---|
| Thrombin | 1019 IU/ml | API (Active Drug Product) |
| Human Serum Albumin | 5.6 mg/ml | Carrier and Stabilizer protein |
| Mannitol | 19.5 mg/ml | Cryoprotectant, stabilizes protein 3D structure |
| Acetate | 18.8 mM | Buffer |
| Calcium | 42 mM | Clot stability |
| Sodium Chloride | 200 mM | Used to dilute Thrombin concentration in dry form of product |

The parameters of the spray dryer were set to the following:

Thrombin sample flow rate: 400 ml/h; Atomizing gas flow rate: 7 l/min; Drying gas flow rate: 600 l/min; Drying gas temperature: 140° C.; Cooling gas flow rate: 100 l/min; Cyclone gas flow rate: 130 l/min; Two-fluid nozzle with tip diameter: 0.4 mm.

3 liters of Composition 59 was spray dried as described above. During the spray drying, the real values of the various spray drying parameters were recorded every 1 minute. 63.25 g spray dried composition was collected in a 200 ml glass bottle designated Bottle #1, and when Bottle #1 was full, 48.41 g spray dried composition was collected in a 200 ml glass bottle designated Bottle #2. After being filled with the dried composition, the bottles were immediately capped and sealed with Parafilm® until analysis was performed.

The average measured spray drying parameters as well as the spray dried thrombin composition attributes were as shown in Table 12:

TABLE 12

| Parameter | Bottle #1 | Bottle #2 |
|---|---|---|
| Atomizing gas flow rate (l/min) | 6.99 ± 0.2 | 7.01 ± 0.17 |
| Drying gas flow rate (l/min) | 600 ± 10 | 600 ± 10 |
| Drying gas temperature (° C.) | 139.97 ± 0.55 | 139.94 ± 0.46 |
| Gas temperature at the drying column outlet (° C.) | 82.48 ± 1.8 | 81.62 ± 1.71 |
| Gas temperature at the inlet of the cyclone (° C.) | 76.32 ± 1.63 | 75.93 ± 1.51 |
| Pressure in the drying column (mBar) | 13.9 ± 0.47 | 13.82 ± 0.48 |
| Pressure drop over the cyclone (mBar) | 46.72 ± 1.06 | 47.25 ± 0.8 |
| Spray dried thrombin-Water content (%) | 2.36 ± 0.08 | |
| Spray dried thrombin-Particle size distribution (μm) | D50-7.70 ± 0.39 D90-15.92 ± 0.64 | |
| Spray dried thrombin activity (IU/mg) | 24.1 ± 0.7 | |
| Spray dried thrombin-Thrombin activity recovery (%) | 98.8 | |
| Spray dried thrombin-mass yield (%) | 91.2 | |

The spray dried thrombin powder obtained was dry with narrow particle size distribution, and most importantly, maintained the thrombin activity of the parent solution.

Example 8: Effect of Drying Gas Temperature on Spray Dried Thrombin Attributes The preferred thrombin composition (composition 8) was spray dried in several spray drying runs, when only the drying gas temperature was changed from run to run:
Thrombin composition flow rate: 7 ml/min
Atomizing gas flow rate: 7 l/min
Drying gas flow rate: 300 l/min
Drying gas temperature: 100, 110, 120, 130, 140, 150, 160, 170, 180 and 190° C.
Cooling gas flow rate: 150 l/min
Cyclone gas flow rate: 300 l/min Dry samples of the spray dried thrombin composition with different drying gas temperatures were collected from the cyclone and the thrombin activity recovery of a respective reconstituted solution was measured as described above. The results of the thrombin activity are shown in FIG. 4 along with the water content of the samples.

Figure 4:
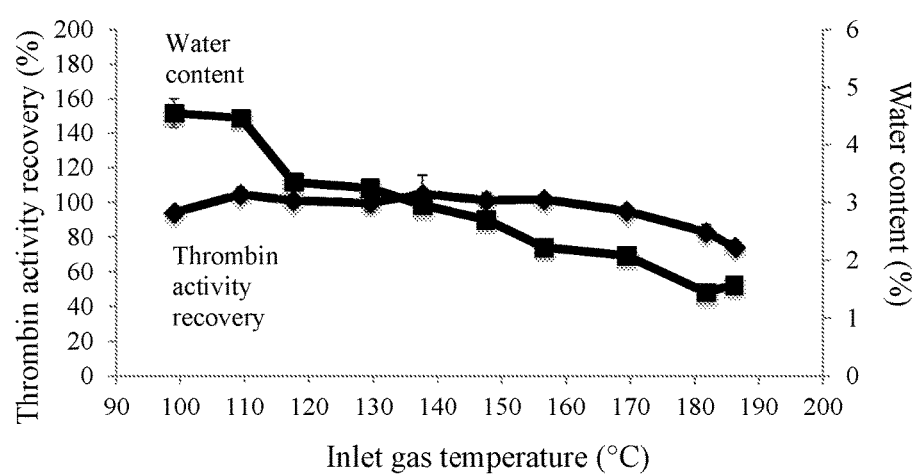
FIG. 4 is a line graph showing the influence of inlet gas temperature on thrombin activity recovery (%) and water content (%) of spray dried thrombin powder.

As shown in FIG. 4, at drying gas temperatures of 170° C. and higher, lower thrombin activity was measured. At lower drying gas temperatures, e.g., 170° C. and less, high thrombin activity was observed. The water content of the spray dried thrombin composition decreased with increased drying gas temperature. At a temperature of 100° C., water content of about 4.5% was obtained. Increasing the temperature up to 190° C. yielded spray dried thrombin powder with water content as low as 1.5%.

Example 9: Effect of Drying Gas Flow Rate on Spray Dried Thrombin Attributes The preferred thrombin composition (composition 8) was spray dried in several spray drying runs, when only the drying gas flow rate was changed from run to run:
Thrombin composition flow rate: 7 ml/min
Atomizing gas flow rate: 7 l/min
Drying gas flow rate: 300, 350, 400, 450, 500 and 550 l/min
Drying gas temperature: 155° C.
Cyclone gas flow rate: Flow rate which supplement to spray dryer total flow rate of 600 l/min (i.e., 300, 250, 200, 150, 100 and 50 l/min).

Samples of dry spray dried thrombin were collected from the cyclone and the thrombin activity recovery of a respective reconstituted solution was measured as described above. The results of the thrombin activity are shown in FIG. 5.

Figure 5:
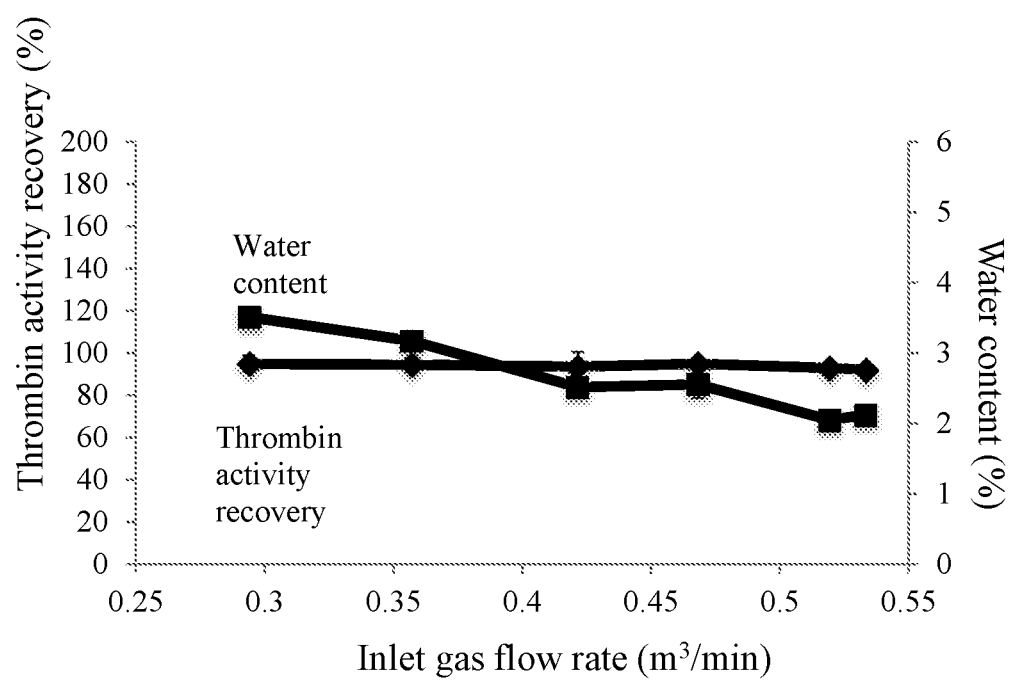
FIG. 5 is a line graph showing the influence of inlet gas flow rate on thrombin activity recovery (%) and water content (%) of spray dried thrombin powder.

As seen in FIG. 5, at all tested drying gas flow rates, high thrombin activity was observed. The water content of the spray dried thrombin decreased with increased drying gas flow rate. At a gas flow rate of 300 l/min, water content of about 3.5% was obtained. Increasing the drying gas flow rate up to 550 l/min yielded spray dried thrombin powder having water content as low as 2%. Taken together, the results indicate that in order to obtain a spray dried thrombin powder with a high thrombin activity recovery and low water content, it is preferable to increase the inlet gas temperature only to a certain limit, e.g. up to about 170° C. Surprisingly, in order to decrease spray dried powder water content without damaging the spray dried thrombin activity recovery, it is recommended to first increase the drying gas flow rate before increasing the drying gas temperature.

Example 10: Production of Fibrin Patches with Lyo-Milled BAC2 and Spray Dried Thrombin The thrombin composition 8 described in Example 1 was spray dried under the conditions described in Example 1. The resulting spray dried thrombin powder recovered from the cyclone was used together with lyophilized-milled BAC2 to produce fibrin patches as described in WO2007117237.

The characteristics of the fibrin patch were analyzed, as shown in Table 13:

TABLE 13

| Parameter | Spray dried thrombin |
|---|---|
| Water content (%) | 2.4 |
| Particle size distribution (μm) | D50 = 8; D90 = 16 |
| Thrombin activity [IU/mg solids] | 24.1 |

The characteristics of the fibrin sealant patch were analyzed as shown in Table 14:

TABLE 14

| Parameter | Fibrin sealant patch made with spray dried thrombin composition |
|---|---|
| water content [%] | 2.1 |
| thrombin activity [IU/cm$^2$] | 36 ± 2.7 |
| total protein [mg/cm$^2$] | 12 |
| Clottable protein [mg/cm$^2$] | 8.4 |
| Friability [weight reduction %] | 8.1 |
| Tissue Peel Test [N/m] | 155 |
| Tensile Strength [N/cm] | 21.4 |

It was seen that the fibrin sealant patch made with the spray dried thrombin powder had low water content (2.1%) and high thrombin activity (36±2.7 IU/cm$^2$).

In the tissue peel test, the adhesion strength of a wetted fibrin sealant patch to a corium tissue substrate was determined by determining the force required to peel the patch from the tissue. The patch made with the spray dried thrombin composition exhibited high adhesion.

Example 11: In Vivo Efficacy of Fibrin Sealant Patch

The time to hemostasis (TTH) of the fibrin sealant patches described in example 10 was tested.

Two pigs of similar size and weight were anesthetized for the entire surgical procedure and the spleens surgically exposed. Five 3 mm deep 15 mm long wounds were made in each one of the two spleens using an appropriate blade and fibrin patches were applied to cover each one of the wounds. The results after 3 minutes are seen in Table 15 and after 10 minutes are seen in Table 16, where a "check" indicates complete hemostasis.

TABLE 15

| Animal #1 - Site Different sites | | | | | Animal #2 - Site Different sites | | | | | |
|---|---|---|---|---|---|---|---|---|---|---|
| Site #1 | Site #2 | Site #3 | Site #4 | Site #5 | Site #1 | Site #2 | Site #3 | Site #4 | Site #5 | % Pass |
| ✓ | ✓ | ✓ | ✓ | ✓ | ✓ | ✓ | ✓ | ✓ | ✓ | 100 |

TABLE 16

| Animal #1 - Different sites | | | | | Animal #2 - Different sites | | | | | % Pass |
|---|---|---|---|---|---|---|---|---|---|---|
| Site #1 | Site #2 | Site #3 | Site #4 | Site #5 | Site #1 | Site #2 | Site #3 | Site #4 | Site #5 | |
| ✓ | ✓ | ✓ | ✓ | ✓ | ✓ | ✓ | ✓ | ✓ | ✓ | 100 |

As can be seen in tables 15 and 16, patches achieved 100% hemostasis within 3 minutes, and no re-bleeding was observed after 10 minutes.

Example 12: Characterization of Spray Dried Thrombin Composition

The thrombin composition 8 of Example 1 was either spray dried under conditions described in Example 1 or lyophilized. The two resulting dried thrombin powders were analyzed for bulk density, tapped density and specific energy (Particle Technology Labs, US) as shown in Table 17.

TABLE 17

|  | Conditioned Bulk Density (gr/ml) | Tapped Density (gr/ml) | Flowability (Specific Energy mJ/gr) |
|---|---|---|---|
| Spray dried composition | 0.46 | 0.58 | 9.52 |
| Lyophilized composition | 0.37 | 0.48 | 20.3 |

The results presented in Table 17 indicate that the spray-dried thrombin powder is denser than the lyophilized thrombin powder. The results in Table 17 also indicate that the spray-dried thrombin powder has a lower specific energy for flowability than the lyophilized thrombin powder, meaning the spray dried thrombin flows more easily. Practically, the spray dried thrombin powder is less likely to cause mechanical interlocking and friction in machinery, for example, reducing the risk of clogging of transfer devices, feeding mechanism and tubing.

The invention claimed is:

1. Spray-dried thrombin powder comprising microcapsules, the microcapsules comprising:
   thrombin spray dried together with a carrier protein and a sugar alcohol, wherein the ratio of thrombin:carrier protein is about 0.85 IU:1 mg to 66,875 IU:1 mg, and wherein the ratio of thrombin:sugar alcohol is 0.75 IU:1 mg to 26,750 IU:1 mg, wherein each of the microcapsules includes the thrombin, carrier protein and sugar alcohol.

2. The spray-dried thrombin powder of claim 1, wherein the ratio of thrombin:carrier protein is from about 110 IU:1 mg to about 285 IU:1 mg, optionally from about 129 IU:1 mg to about 219 IU:1 mg.

3. The spray-dried thrombin powder of claim 1, wherein the carrier protein comprises albumin.

4. The spray-dried thrombin powder of claim 1, wherein the carrier protein is albumin and the sugar alcohol is mannitol, wherein the ratio of thrombin:albumin is about 0.85 IU:1 mg to 66,875 IU:1 mg, and wherein the ratio of thrombin:mannitol is 0.75 IU:1 mg to 26,750 IU:1 mg.

5. The spray-dried thrombin powder of claim 4, wherein the ratio of thrombin:albumin is from about 110 IU:1 mg to about 285 IU:1 mg, optionally from about 129 IU:1 mg to about 219 IU:1 mg.

6. The spray-dried thrombin powder of claim 4, wherein the ratio of thrombin:mannitol is from about 40 IU:1 mg to about 64 IU:1 mg.

7. The spray-dried thrombin powder of claim 1, comprising from about 0.001% to about 5% w/w thrombin.

8. The spray-dried thrombin powder of claim 1, comprising less than about 3% w/w water.

9. The spray-dried thrombin powder of claim 1, having a particle size distribution of D50 of from about 5 to about 13 μm and D90 of from about 15 to about 25 μm.

10. An aqueous composition suitable for use in preparing thrombin microcapsules, the aqueous composition comprising:
    thrombin, a carrier protein and a sugar alcohol, wherein the ratio of thrombin:carrier protein is about 1.6 IU:1 mg to 5,000 IU:1 mg, and wherein the ratio of thrombin:sugar alcohol is 2 IU:1 mg to 1500 IU:1 mg.

11. A method for preparing thrombin microcapsules, the method comprising the steps of: mixing thrombin, a carrier protein and a carbohydrate in an aqueous solution wherein the ratio of thrombin:carrier protein is about 1.6 IU:1 mg to 5000 IU:1 mg, and wherein the ratio of thrombin:carbohydrate is 2 IU:1 mg to 1500 IU:1 mg; and
    spray drying the aqueous solution.

12. The method of claim 11, wherein the spray drying comprises:
    introducing the aqueous solution into a spray drying device;
    producing droplets from the aqueous solution introduced into the device by using an atomizing gas flow; and
    evaporating water from the droplets by a drying gas flow, thereby preparing thrombin microcapsules.

13. The method of claim 11, the aqueous solution comprising:
    from about 800 to about 1200 IU/ml thrombin;
    from about 0.5 to about 0.65% w/v carrier protein;
    from about 1.85 to about 2.05% w/v carbohydrate;
    from about 38 to about 42 mM calcium;
    from about 18.0 to about 20.0 mM acetate; and
    about 60-240 mM sodium chloride,
    the solution having a density of from about 1.01 to about 1.03 g/ml.

14. Spray-dried thrombin microcapsules prepared according to the method of claim 11, wherein the carbohydrate comprises a sugar alcohol, and wherein each of the microcapsules includes the thrombin, carrier protein and sugar alcohol.

15. A matrix comprising the spray-dried thrombin powder of claim 1 and/or spray-dried thrombin microcapsules of claim 14.

16. The matrix of claim 15, further comprising a fibrinogen powder.

17. The matrix of claim 16, wherein the fibrinogen powder is prepared by freeze-drying.

18. A kit comprising a container comprising the spray-dried thrombin powder of claim 1 and/or the spray-dried thrombin microcapsules of claim 14.

* * * * *